US009678005B1

(12) United States Patent
Yoon

(10) Patent No.: US 9,678,005 B1
(45) Date of Patent: Jun. 13, 2017

(54) DEVICES AND METHODS FOR DETECTION OF MICROORGANISMS

(71) Applicant: ARIZONA BOARD OF REGENTS ON BEHALF OF THE UNIVERSITY OF ARIZONA, Tucson, AZ (US)

(72) Inventor: Jeong-Yeol Yoon, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 1084 days.

(21) Appl. No.: 13/644,622

(22) Filed: Oct. 4, 2012

Related U.S. Application Data

(63) Continuation-in-part of application No. 12/630,069, filed on Dec. 3, 2009, and a continuation-in-part of
(Continued)

(51) Int. Cl.
*G01N 21/47* (2006.01)
*B01L 3/00* (2006.01)
(Continued)

(52) U.S. Cl.
CPC .............. *G01N 21/47* (2013.01); *B01L 3/502* (2013.01); *B01L 2300/0816* (2013.01);
(Continued)

(58) Field of Classification Search
None
See application file for complete search history.

(56) References Cited

U.S. PATENT DOCUMENTS 4,521,521 A * 6/1985 Abbott ............. G01N 33/54313
250/574
5,862,273 A 1/1999 Pelletier
(Continued)

FOREIGN PATENT DOCUMENTS

WO 2008/049187 A1 5/2008

OTHER PUBLICATIONS

Han (2007) Anal Chim ACTA p. 252-259.*
(Continued)

*Primary Examiner* — Melanie Y Brown
*Assistant Examiner* — Richard Moerschell
(74) *Attorney, Agent, or Firm* — Nguyen & Tarbet Patent Law Firm

(57) ABSTRACT

The present invention features methods and devices for microorganisms through detecting Mie light scattering from immunoagglutinated beads. The methods feature providing a first bead suspension with antibody specific for the microorganism conjugated to beads; mixing the first bead suspension with a sample to form a first mixture; irradiating the first mixture with first incident light; detecting forward light scattering at a first angle with respect to the first incident light, where the first angle being between about 30 to 60 degrees; determining I from the light scattering; providing a second bead suspension with no antibody and simultaneously measuring $I_0$ in a similar manner; comparing I with $I_0$. All light scattering measurements may be made in a two-well slide or a Y-channel microfluidic device.

3 Claims, 12 Drawing Sheets

Related U.S. Application Data application No. 13/458,650, filed on Apr. 27, 2012, now Pat. No. 9,562,855.

(60) Provisional application No. 61/200,702, filed on Dec. 3, 2008.

(51) Int. Cl.

*G01N 33/58* (2006.01)
*G01N 33/569* (2006.01)
*G01N 33/543* (2006.01)

(52) U.S. Cl.

CPC ..... *G01N 33/54313* (2013.01); *G01N 33/569* (2013.01); *G01N 33/56911* (2013.01); *G01N 33/585* (2013.01); *G01N 2021/4704* (2013.01); *G01N 2021/4707* (2013.01); *G01N 2021/4711* (2013.01)

(56) References Cited

U.S. PATENT DOCUMENTS 5,943,130 A * 8/1999 Bonin ................ G01N 15/0205 356/237.5
6,040,906 A 3/2000 Harhay
6,689,572 B1 2/2004 Huang et al.
7,034,325 B2 4/2006 Besesty et al.
7,118,676 B2 10/2006 Mueth et al.
7,300,631 B2 11/2007 Miller et al.
7,338,813 B2 3/2008 Obana
7,576,861 B2 8/2009 Gilbert et al.
7,738,099 B2 * 6/2010 Morrell et al. ............... 356/336
2002/0064867 A1 * 5/2002 Clark ................... G01N 21/253 435/288.7
2002/0180963 A1 12/2002 Chien et al.
2003/0194818 A1 * 10/2003 Hechinger ........... C12Q 1/6816 436/513
2004/0056197 A1 * 3/2004 Davidson ........... G01N 21/3577 250/339.1
2004/0108462 A1 * 6/2004 Besesty et al. ............... 250/343
2004/0176320 A1 * 9/2004 Natunen .............. A61K 31/739 514/54
2005/0068536 A1 * 3/2005 Schwabe ........... B01L 3/502715 356/436
2006/0129327 A1 * 6/2006 Kim ......................... B82Y 5/00 702/19
2006/0172370 A1 8/2006 Hirleman, Jr. et al.
2007/0279627 A1 12/2007 Tack et al.
2008/0032281 A1 2/2008 Lea et al.
2010/0136610 A1 6/2010 Yoon et al.
2011/0207152 A1 8/2011 Shen et al.

OTHER PUBLICATIONS

Han (2007) Anal Chim ACTA 584 p. 252-259.*

Han et al.; The enhanced diffusional mixing for latex immunoagglutination assay in a microfluidic device; ScienceDirect; Analytica Chimica Acta 584 (2007); 252-259.

Han et al.; Single cell level detection of *Escherichia coli* in microfluidic device, Biosensors and Biolectronics, vol. 23, No. 8, pp. 1303-1306 [online], Dec. 4, 2007 (Dec. 4, 2007), Retriefed from the internet: www.sciencedirect.com.

Lucas et al., "Lab-on-a-chip immunoassay for multiple antibodies using microsphere light scattering and quantum dot emission", Aug. 11, 2007, Biosensors & Bioelectronics, 23, pp. 675-681.

Lucas et al., "Latex immunoagglutination assay for a vasculitis market in a microfluidic device using static light scattering detection", Dec. 1, 2006, Biosensors and Bioelectronics, 22, pp. 2216-2222.

* cited by examiner

DEVICES AND METHODS FOR DETECTION OF MICROORGANISMS

CROSS REFERENCE

This application is a continuation-in-part of U.S. patent application Ser. No. 13/458,650 filed Apr. 27, 2012, which is a continuation-in-part of U.S. patent application Ser. No. 12/630,069 filed Dec. 3, 2009, which claims priority to U.S. Provisional Application Ser. No. 61/200,702 filed Dec. 3, 2008, the specification of which is incorporated herein by reference in its entirety.

FIELD OF THE INVENTION

The present invention is directed to methods and devices for detection of microorganisms, more particularly to devices and methods for detecting Mie forward light scattering of the microorganisms and antibody-conjugated beads.

BACKGROUND OF THE INVENTION

Illnesses caused by foodborne pathogens range from mild gastrointestinal infections to life-threatening hemorrhagic colitis, haemolytic uremic syndrome, and thrombotic thrombocytopenic purpura. Outbreaks of foodborne pathogens have recently increased in fresh produce. Conventional detection methods often require sample preparation (cell lysis and filtration) and concentration (cell culturing), which can be time consuming.

The present invention features methods and devices for detecting microorganisms. As used herein, the term "microorganisms" includes bacteria, archaea, protists, fungi, microscopic plants (e.g., algae), microscopic animals (e.g., plankton), and viruses. For example, an embodiment wherein a device detects a microorganism includes a device that detects a bacteria or a virus, etc. In some embodiments, the device of the present invention is a microfluidic device. The device may quantify increased light scattering due to immunoagglutination in the device (e.g., immunoagglutination in a sample in the device).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a method of detecting a microorganism. The method may comprise providing a first bead suspension, wherein an antibody specific for a first microorganism is attached to beads in the first bead suspension; mixing the first bead suspension with a portion of a sample to form a first mixture, wherein the sample is being tested for the presence of the first microorganism; irradiating the first mixture with first incident light; detecting a forward scattered light scattered by the first mixture, the forward scattered light is at a first angle with respect to the first incident light, the first angle being between about 30 to 60 degrees; determining/from the scattering of first incident light by the first mixture; providing a second bead suspension, wherein an antibody is not attached to beads in the second bead suspension; mixing the second bead suspension with a portion of the sample to form a second mixture; irradiating the second mixture with a second incident light; detecting a forward scattered light scattered by the second mixture, the forward scattered light is at a second angle with respect to the second incident light, the second angle being the same as the first angle; determining $I_0$ from the scattering of incident light by the second mixture; and comparing I with $I_0$.

In some embodiments, the beads in the first bead solution and the second bead solution have a diameter between about 200 to 1,000 nm. In some embodiments, the beads in the first bead solution and the second bead solution have a diameter of about 920 nm. In some embodiments, the beads in the first bead solution and the second bead solution are constructed from a material comprising polystyrene. In some embodiments, the beads in the first bead solution and the second bead solution comprise a plurality of carboxyl groups disposed on an outer surface. In some embodiments, the beads in the first bead solution and the second bead solution comprise at least 5 carboxyl groups per $nm^2$ surface area. In some embodiments, the carboxyl groups are polyacrylic acid (PAA) or polymethacrylic acid (PMAA). In some embodiments, the antibody is a polyclonal antibody or a monoclonal antibody to the microorganism.

In some embodiments, the microorganism is a bacterium, an archaea, a protist, a fungus, a microscopic plant, a microscopic animal, or a virus. In some embodiments, the bacteria includes *Escherichia coli, Salmonella typhimurium, Acetobacter aurantius, Acinetobacter baumannii, Actinomyces Israelii, Agrobacterium radiobacter, Agrobacterium tumefaciens, Azorhizobium caulinodans, Azotobacter vinelandii, Anaplasma phagocytophilum, Anaplasma marginale, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaninogenicus* (e.g., *Prevotella melaninogenica*), *Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae* (e.g., *Chlamydia pneumoniae*), *Chlamydophila psittaci* (e.g., *Chlamydia psittaci*), *Clostridium botulinum, Clostridium difficile, Clostridium perfringens* (e.g., *Clostridium welchii*), *Clostridium tetani, Corynebacterium diphtheriae, Corynebacterium fusiforme, Coxiella bumetii, Ehrlichia chaffeensis, Enterobacter cloacae, Enterococcus avium, Enterococcus durans, Enterococcus faecalis, Enterococcus faecium, Enterococcus gallinarum, Enterococcus maloratus, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Myco-*

*plasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Smreptococcus mutans, Streptococcus oralis, Stayyereyofhia mioms, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Yersinia enterocolitica, Yersinia pestis* or, *Yersinia pseudotuberculosis.*

In some embodiments, the light has a wavelength between about 320 to 800 nm. In some embodiments, the light has a wavelength of about 375 nm. In some embodiments, the light is generated from a light emitting diode (LED). In some embodiments, the light has an intensity of less than about 100 μW. In some embodiments, the light has an intensity of about 45 μW. In some embodiments, the first angle is about 45 degrees. In some embodiments, the first angle is between about 30 to 60 degrees. In some embodiments, the method further comprises calculating a ratio of $I/I_0$, wherein a ratio of greater than 1 indicates the presence of the microorganism in the sample. In some embodiments, the method further comprises calculating a ratio of $I/I_0$, wherein a difference between I and $I_0$ is calculated by subtracting of $I_0$ from of I, wherein a difference of greater than 0 indicates the presence of the microorganism in the sample.

Both I and $I_0$ are light intensities of forward light scattering, as can be measured by a portable spectrometer in a large-scale device, or an electrical circuit and an LCD display in a small-scale device. Light scattering intensity (I) is a function of wavelength of an incident beam (λ), scattering angle (θ), refractive index of beads (n) and diameter of beads (d). In large-scale device, both I and $I_0$ varies upon integration time and the spectrometer used. In a small-scale device, they depend on the power of laser diode used, the sensitivity of photodiode used, the gain of op-amp circuit, and programming in Arduino board. For both large- and small-scale devices, consequently, both I and $I_0$ have arbitrary unit (AU). In some embodiment, both I and $I_0$ have a range from 0 to 65535 (16-bit) or 0 to 4095 (12-bit). Mie simulations can be used to determine the optimal parameters (lambda, n and d) for the assay that maximizes I of immunoagglutinated beads and minimizes I of the sample matrix (e.g., tissue fragments of iceberg lettuce), which can be experimentally validated. This introduces a powerful method for detecting foodborne pathogens in many different food sample matrices.

The present invention also features an apparatus for detecting a microorganism. The apparatus may comprise a first well in a first light transparent base, the well holds a first mixture comprising a first bead suspension and a portion of a sample that potentially comprises the microorganism, the beads in the first bead suspension are conjugated with an antibody specific for the microorganism; a first light disposed under the first well, the first light is for irradiating the first mixture with a first incident light; a first detector disposed above the first well, the first detector is capable of detecting a first forward scattered light which is scattered by the first mixture as the first mixture is irradiated by the first incident light; a second well in a second light transparent base, the well holds a second mixture comprising a second bead suspension and a portion of the sample that potentially comprises the microorganism, the beads in the second bead suspension are not conjugated with an antibody; a second light disposed under the second well, the second light is for irradiating the second mixture with a second incident light; a second detector disposed above the second well, the second detector is capable of detecting a second forward scattered light which is scattered by the second mixture as the second mixture is irradiated by the second light; a processing unit operatively connected to both the first detector and the second detector, the processing unit is configured to calculate an I value from a first input signal from the first detector and an $I_0$ value from a second input signal from the second detector; a display component for displaying I and $I_0$; and a power source operatively connected to the first light, the first detector, the second light, the second detector, and the processing unit.

In some embodiments, the processing unit is also configured to calculate a ratio of $I/I_0$ or a difference between I and $I_0$; and the display component can display the ratio of $I/I_0$ or the difference between I and $I_0$. In some embodiments, the processing unit comprises an operational amplifier circuit configured to amplify the signals produced by the first and second detectors, respectively. In some embodiments, the processing unit comprises an operational amplifier circuit configured to generate the I value from the first input signal from the first detector and the $I_0$ value from the second input signal from the second detector. In some embodiments, the processing unit comprises an operational amplifier circuit configured to calculate a ratio of $I/I_0$ or a difference between I and $I_0$. In some embodiments, the processing unit comprises an analog-digital converter operatively connected to an operational amplifier circuit, the analog-digital converter converts an analog input from the operational amplifier circuit to a digital signal and sends the digital signal to the display.

In some embodiments, the first well and the second well have a diameter of about 18 mm. In some embodiments, the first well and the second well have a diameter between about 2 to 30 mm. In some embodiments, the first well and the second well have a depth of about 800 μm. In some embodiments, the first well and the second well have a depth between about 100 to 1,500 μm. In some embodiments, the light is a 650 nm light emitting diode (LED) or laser diode. In some embodiments, the light is a 320-800 nm light emitting diode (LED) or laser diode. In some embodiments, the detector is a photodiode. In some embodiments, the photodiode is an Avalanche photodiode (APD). In some embodiments, the operational amplifier is a quadruple op-amp LM324. In some embodiments, the processing unit is an Arduino prototyping board. In some embodiments, the power source is one or more batteries.

BRIEF DESCRIPTION OF THE DRAWINGS

FIG. 3A shows the light scattering intensities detected from a microfluidic device immunoassay, FIG. 3B shows the light scattering intensities detected from a two-wall slide immunoassay. All data are the intensity difference of scattered light with and without analyte. (Note: Error bars are standard deviations. The * symbol represents a significant difference from blank signal).

An integrated version of the device shown in FIG. 2 (large-scale system) is shown in FIGS. 7A and 7B. FIGS. 1A and 1B), fiber optics for light source and detector and a fixed positioning stage (FIG. 10).

FIG. 12A shows vegetables being grinded. FIG. 12B shows the grinded vegetables being diluted with a solution (e.g., PBS). FIG. 12C shows the samples after filtration.

DESCRIPTION OF PREFERRED EMBODIMENTS

Figure 1A:
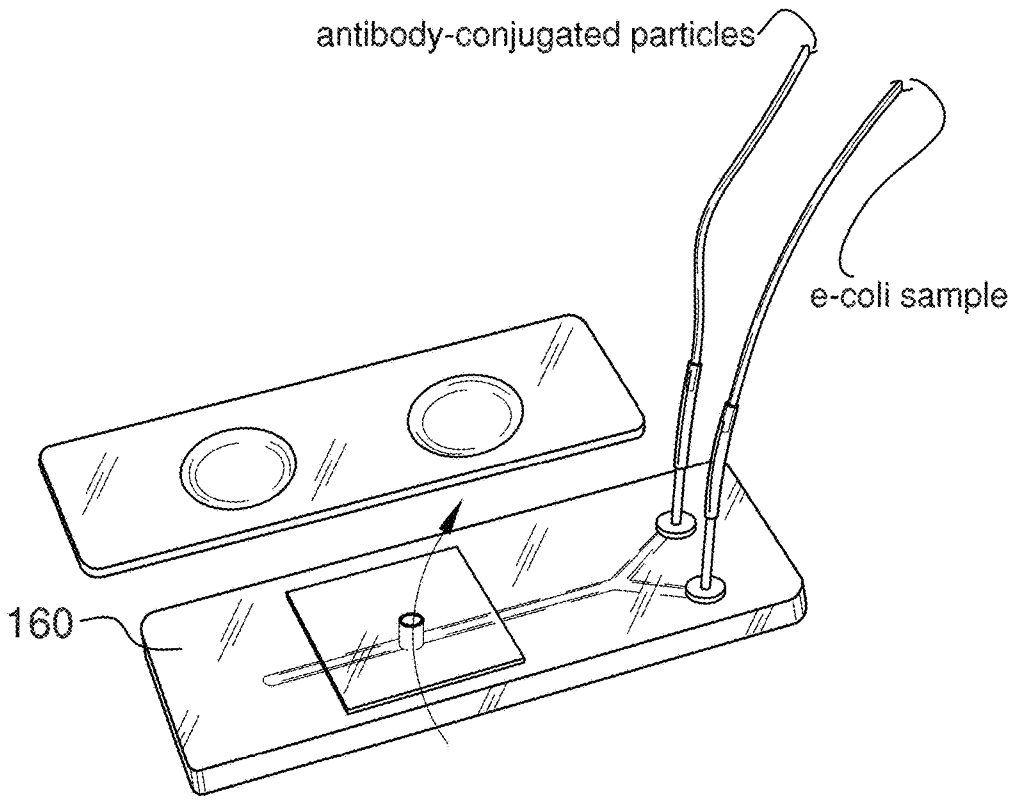
FIG. 1A is a perspective view of examples of a two-well slide and a Y-shape microfluidic device.

Referring now to FIG. 1-14, the present invention features methods and devices for detecting microorganisms in samples (e.g., food/vegetable samples, fluid samples, etc.).

In some embodiments, the microorganism is a bacterium, an archaea, a protist, a fungus, a microscopic plant, a microscopic animal, or a virus. Bacteria may include *Escherichia coli, Salmonella typhimurium, Acetobacter aurantius, Acinetobacter baumannii, Actinomyces Israelii, Agrobacterium radiobacter, Agrobacterium tumefaciens, Azorhizobium caulinodans, Azotobacter vinelandii, Anaplasma phagocytophilum, Anaplasma marginale, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaninogenicus* (e.g., *Prevotella melaninogenica*), *Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae* (e.g., *Chlamydia pneumoniae*), *Chlamydophila psittaci* (e.g., *Chlamydia psittaci*), *Clostridium botulinum, Clostridium difficile, Clostridium perfringens* (e.g., *Clostridium welchii*), *Clostridium tetani, Corynebacterium diphtheriae, Corynebacterium fusiforme, Coxiella bumetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis,*

*Streptococcus ferus, Streptococcus gallinarum, Streptococcus lactis, Streptococcus mitior, Streptococcus mitis, Smreptococcus mutans, Streptococcus oralis, Stayyereyofhia mioms, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Yersinia enterocolitica, Yersinia pestis, Yersinia* or *pseudotuberculosis*.

The *Escherichia coli* strain may include strain K12, O157:h7, 042, 101-1,1180, 1357, 1412, 1520, 1827-70, 2362-75, 3431, 53638, 83972, 929-78, 98NK2, ABU 83972, B, B088, B171, B185, B354, B646, B7A, C, c7122, CFT073, DH1, DH5[alpha], E110019, E128010, E74/68, E851171, EAEC 042, EPECa11, EPECa12, EPECa14, ETEC, H10407, F11, F18+, FVEC1302, FVEC1412, GEMS_EPEC1, HB101, HT115, KO11, LF82, LT-41, LT-62, LT-68, MS 107-1, MS 119-7, MS 124-1, MS 145-7, MS 79-2, MS 85-1, NCTC 86, Nissle 1917, NT:H19, NT:H40, NU14, O103:H2, O103:HNM, O103:K+, O104:H12, 0108:H25, O109:H9, O111:H−, O111:H19, O111:H2, O111:H21, O111:NM, O115:H−, O115:HMN, O115:K+, O119:H6, O119:UT, O124:H40, O127a:H6, O127:H6, O128:H2, O131:H25, O136:H−, O139:H28 (strain E24377A/ETEC), O13:H11, O142:H6, O145:H−, O153:H21, O153:H7, O154:H9, O157:12, O157:H−, O157:H12, O157:H43, O157:H45, O157:H7 EDL933, O157:NM, O15:NM, O177:H11, O17:K52:H18 (strain UMN026/ExPEC), O180:H−, O1:K1/APEC, O26, O26:H−, O26:H11, O26:H11:K60, O26:NM, O41:H−, O45:K1 (strain S88/ExPEC), O51:H−, O55:H51, O55:H6, O55:H7, O5:H−, O6, O63:H6, O63:HNM, O6:K15:H31 (strain 536/UPEC), O7:K1 (strain IAI39/ExPEC), O8 (strain IAI1), O81 (strain ED1a), O84:H−, O86a:H34, O86a:H40, O90:H8, O91:H21, O9:H4 (strain HS), O9:H51, ONT:H−, ONT:H25, OP50, Orough:H12, Orough:H19, Orough:H34, Orough:H37, Orough:H9, OUT:H12, OUT:H45, OUT:H6, OUT:H7, OUT:HNM, OUT:NM, RN587/1, RS218, 55989/EAEC, B/BL21, B/BL21-DE3, SE11, SMS-3-5/SECEC, UTI89/UPEC, TA004, TA155, TX1999, Vir68.

Methods of Detecting Microorganisms

The present invention features a method of detecting a microorganism, the method comprises providing a first bead suspension (with beads 110). The beads 110 in the first bead suspension are conjugated with an antibody 120 (e.g., see FIG. 4) specific for the microorganism. The method further comprises mixing the first bead suspension with a portion of a sample that is being tested for the presence (and/or for a level of) a microorganism. The first bead suspension and the sample together form a first mixture. The mixing of the sample and the bead suspension occurs via diffusional mixing, hence mechanical mixing (e.g., vibration, vortexing or shaking) is not required. This spontaneous mixing is made possible via use of highly carboxylated polystyrene beads. Generally, the microorganism 105 may bind to the specific antibody, causing agglutination to occur (see FIG. 5).

Figure 6:
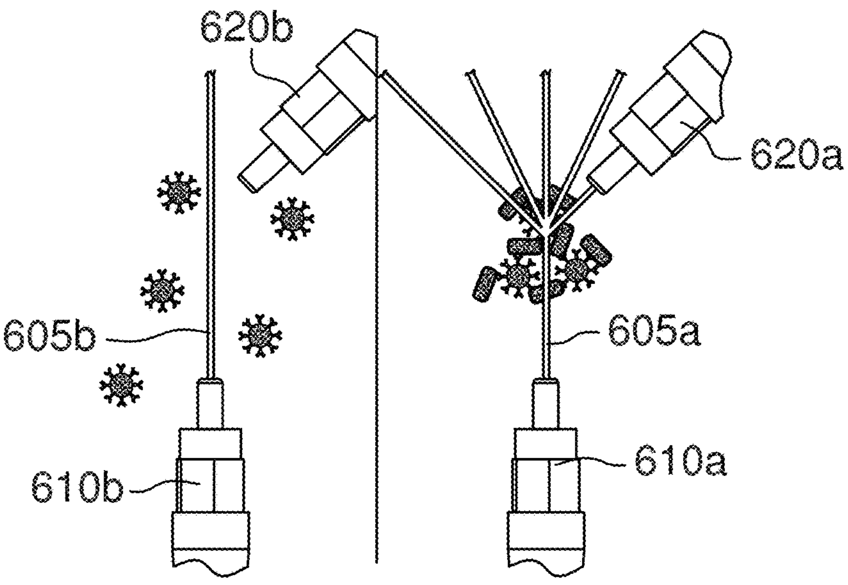
FIG. 6 is a side view of an incident beam of light to a mixture and detectors for capturing Mie forward scattering by the mixtures. On the left side of the figure, the mixture scatters minimum light (e.g., no agglutination has occurred in this sample). On the right side of the figure, increased light scattering is made by the mixture and the detector captures a portion of the forward scattered light.

The method further comprises irradiating the first mixture with a light (e.g., a first incident light) and detecting a forward scattered light scattered by the first mixture (see FIG. 6, for example the right side of the figure). The forward scattered light scattered by the first mixture that is detected may be at a first angle with respect to the light (e.g., first incident light). The first angle may be between about 30 to 60 degrees. The method further comprises determining/from the forward scattered light scattered by the first mixture.

The method further comprises providing a second bead suspension with beads. The beads in the second bead suspension are not conjugated with an antibody. The second bead suspension is mixed with a portion of the sample to form a second mixture. Like the first mixture, the mixing of the sample and the second bead suspension occurs via diffusional mixing. Generally, the microorganism in the sample does not cause agglutination to occur because the second mixture lacks antibody (e.g., antibody specific for the microorganism).

The method further comprises irradiating the second mixture with a light (e.g., a second incident light) and detecting a forward scattered light scattered by the second mixture (see FIG. 6, for example the left side of the figure). The forward scattered light scattered by the second mixture that is detected may be at a second angle with respect to the light (e.g., the second incident light), the second angle being the same as the first angle.

The method further comprises determining $I_0$ from the forward scattered light that is detected from the second sample and comparing I with $I_0$. In some embodiments, a ratio of $I/I_0$ is calculated. In some embodiments, a ratio of $I/I_0$ that is greater than 1 indicates the presence of the microorganism in the sample. In some embodiments, a difference between I and $I_0$ is calculated by subtracting of $I_0$ from of I. In some embodiments, a difference of greater than 0 indicates the presence of the microorganism in the sample.

I and $I_0$ are obtained directly from a portable spectrometer (in a large-scale system) as digital signals from 0 to 65535. I and $I_0$ are obtained from a LCD display, which are processed by an op-amp circuit and an Arduino board (in a small-scale system). These are arbitrary numbers, and can be configured to represent a meaningful number (e.g., in colony forming units per ml or CFU/ml) by adjusting the integration time of a portable spectrometer (in large-scale system) or the gain of an op-amp circuit (in small-scale system).

Figure 14:
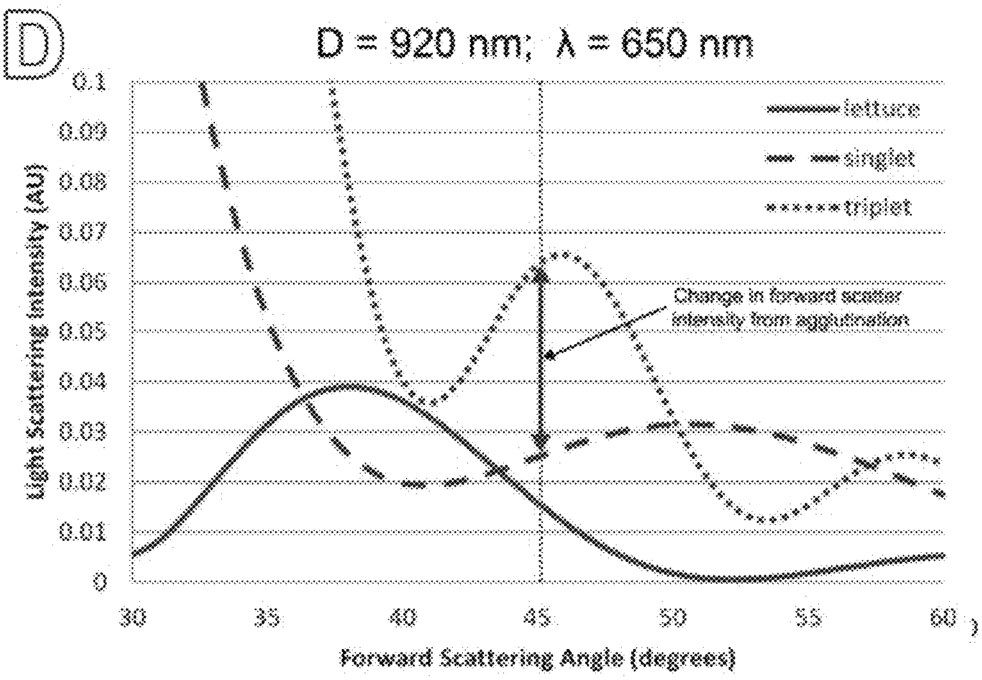
FIG. 14 exhibits the Mie scatter properties of the filtered lettuce particles (n=1.425) and the 920 nm microparticles (n=1.59) as singlets and triplets using a 650 nm light source.

FIG. 14 exhibits the Mie scatter properties of the filtered lettuce particles (n=1.425) and the 920 nm microparticles (n=1.59) as singlets and triplets using a 650 nm light source. The use of a triplet model for representing agglutination in the experimental simulations was based on the microscopic image analyses of immunoagglutinated particles in the presence of *E. coli*, where the triplets were the most significant. The simulations take into account the decrease in particle concentration from agglutination. Thus, the triplet model results in ⅓ the particle concentration as the singlet model. At a forward scattering angle of 45°, the 920 nm singlet shows a minimal increase in light scatter intensity over the lettuce particles (~0.01 AU), and the 920 nm triplet shows a significant increase over the lettuce particles (~0.05 AU) as well as the 920 nm singlet (~0.04 AU). These simulations demonstrate that the detection of *E. coli* in a real biological matrix under these minimal pretreatment steps for ground iceberg lettuce is possible by choosing an appropriate scattering angle. They also reveal that the forward light scattering angle is an essential optimization parameter, since a scattering angle of 5° in either direction from 45° would have no detectable change in light scatter intensity and substantial scattering from lettuce particles.

Antibody-Conjugated Beads

The beads 110 (e.g., microspheres) in the first bead suspension and/or the second bead suspension may be constructed in a variety of sizes and from a variety of materials. For example, in some embodiments, the beads 110 have a diameter between about 200 to 1,000 nm. In some embodiments, the beads 110 have a diameter of about 920 nm. In some embodiments, the beads 110 are constructed from a material comprising a hydrophobic material (e.g., a hydrophobic core), for example a material comprising polystyrene (e.g., a polystyrene core). In some embodiments, the beads 110 are constructed from a material comprising a hydrophilic material (e.g., a hydrophilic outer surface), for example a material comprising one or more carboxyl groups (e.g., a plurality of carboxyl groups disposed on an outer surface). The beads 110, for example the outer surfaces of the beads 110, may comprise at least 5 carboxyl groups per $nm^2$ surface area. The carboxyl groups may include but are not limited to polyacrylic acid (PAA) or polymethacrylic acid (PMAA). Beads may be obtained, for example, from Bangs Laboratories, Fishers, Ind.

Figure 4:
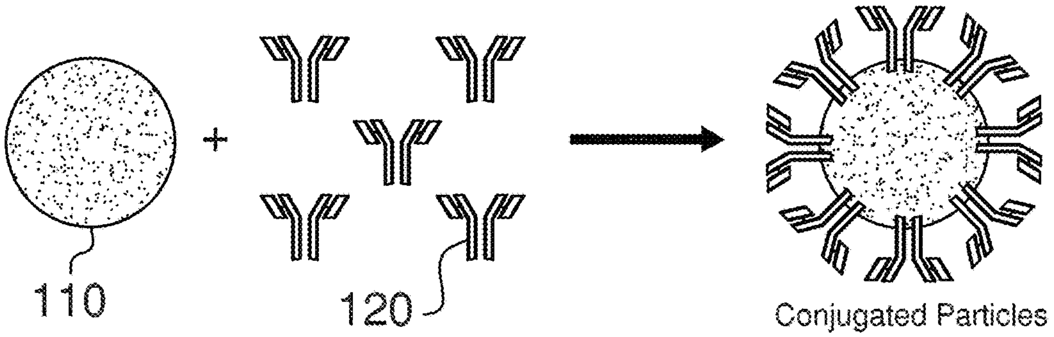
FIG. 4 is a schematic representation of antibody conjugation to a bead (e.g., microsphere).
Figure 5:
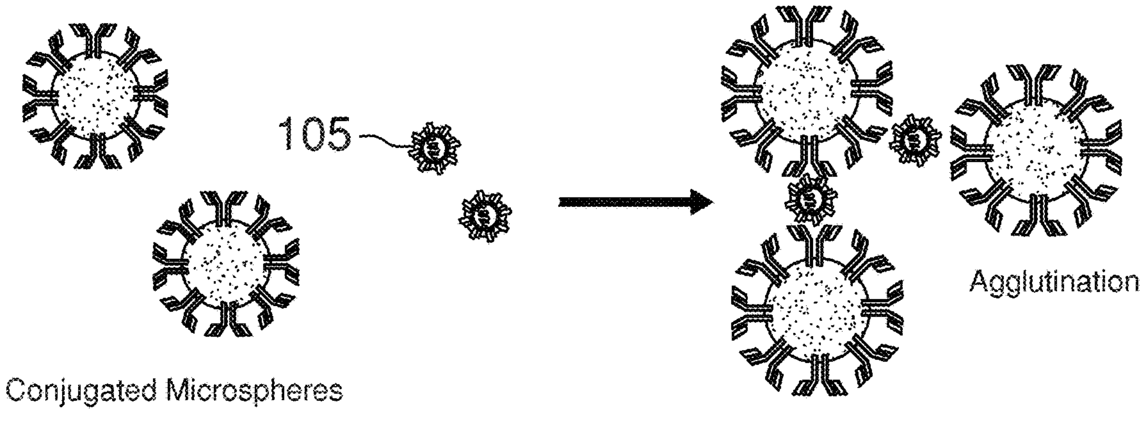
FIG. 5 is a schematic representation of immunoagglutination from mixing a target (e.g., microorganism) and antibody-conjugated beads.

The beads 110 in the first bead suspension are conjugated with an antibody 120 specific for the microorganism 105 (see FIG. 4). Antibody conjugation can occur either via passive adsorption or covalent binding, although in some examples, covalent binding may be preferred. These protocols are available in public domain, for example, http://www.bangslabs.com/files/bangs/docs/pdf/201.pdf. In some embodiments, the antibody 120 is a monoclonal or a polyclonal antibody.

Light

The forward light scattering by the first mixture that is detected is at a first angle with respect to the light (e.g., first incident light 605*a*). The forward light scattering by the second mixture that is detected is at a second angle with respect to the light (e.g., second incident light 605*b*), wherein the second angle is about the same as the first angle. The first angle and the second angle may be between about 30 to 60 degrees. In some embodiments, the first angle and the second angle are about 45 degrees.

In some embodiments, the light (e.g., first incident light 605*a*, second incident light 605*b*) has a wavelength between about 320 to 800 nm. In some embodiments, the light (e.g., first incident light 605*a*, second incident light 605*b*) has a wavelength of about 375 nm. In some embodiments, a wavelength significantly smaller than the particle size (e.g., diameter) is preferred to induce Mie light scattering, which depends primarily on the particle size. In some embodiments, an ultraviolet wavelength is used, for example, because of the energy it provides. Without wishing to limit the present invention to any theory or mechanism, it is believed that in some cases ultraviolet wavelengths may be advantageous because they have more energy and thus may penetrate a sample more efficiently.

In some embodiments, the light (e.g., first incident light 605*a*, second incident light 605*b*) is generated from a light emitting diode (LED) (e.g., continuous LED) or a laser diode, and may be delivered via fiber optics in some embodiments. In some embodiments, the light (e.g., first incident light 605*a*, second incident light 605*b*) has an intensity of less than about 100 μW. In some embodiments, the light (e.g., first incident light 605*a*, second incident light 605*b*) has an intensity of about 45 μW.

Immunoagglutination in the mixtures (e.g., in the first mixture) causes Mie scattering of incident light. Mie scattering refers to a solution of Maxwell's equations for the scattering of electromagnetic radiation by spherical particles. Mie scattering predominates at $d \geq \lambda$ (thus shorter wavelength, e.g., ultraviolet, is preferred for submicron beads). Mie scattering is generally dependent on the size of the particle. The highest amount of scatter is generally at 0 degrees from the incident light; however, typically one cannot differentiate incident from scatter at 0 degrees. In some embodiments, an alternate angle to detect scattered light is about 45 degrees from the incident light, or between about 30 to 60 degrees.

Sample Preparation

Samples, for example food samples (e.g., vegetable samples), may be prepared in a variety of ways. A vegetable sample 990 may be chopped up and added to a buffer, for example, at a ratio of about 1:1 to 1:3 (vegetable to buffer). The sample may be further diluted as needed. In some embodiments, the sample is then filtered with a common cloth or tissue component (e.g., KimWipes, Kimberly-Clark Corporation). Without wishing to limit the present invention to any theory or mechanism, the process of filtering the sample with a tissue component is advantageous because it helps to quickly and easily remove large chunks or particles in the sample. This may be faster (and possibly cheaper) than if a filtration apparatus or procedures are used (e.g., centrifugation, etc.).

Apparatuses for Detecting Microorganisms

Figure 2:
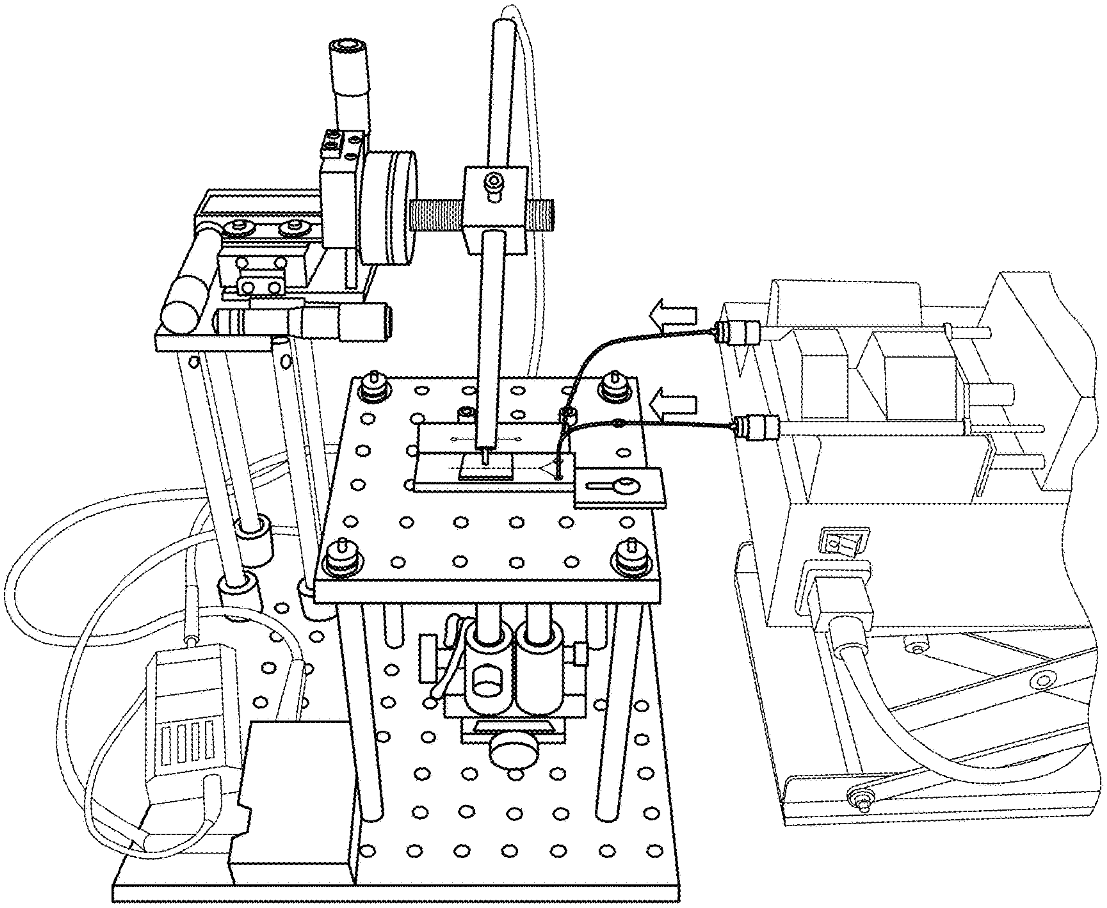
FIG. 2 is an example of an experimental setup with a microfluidic device. A portable spectrometer and a UV (375 nm) light source is used in this example for optical fiber detection.
Figure 3A:
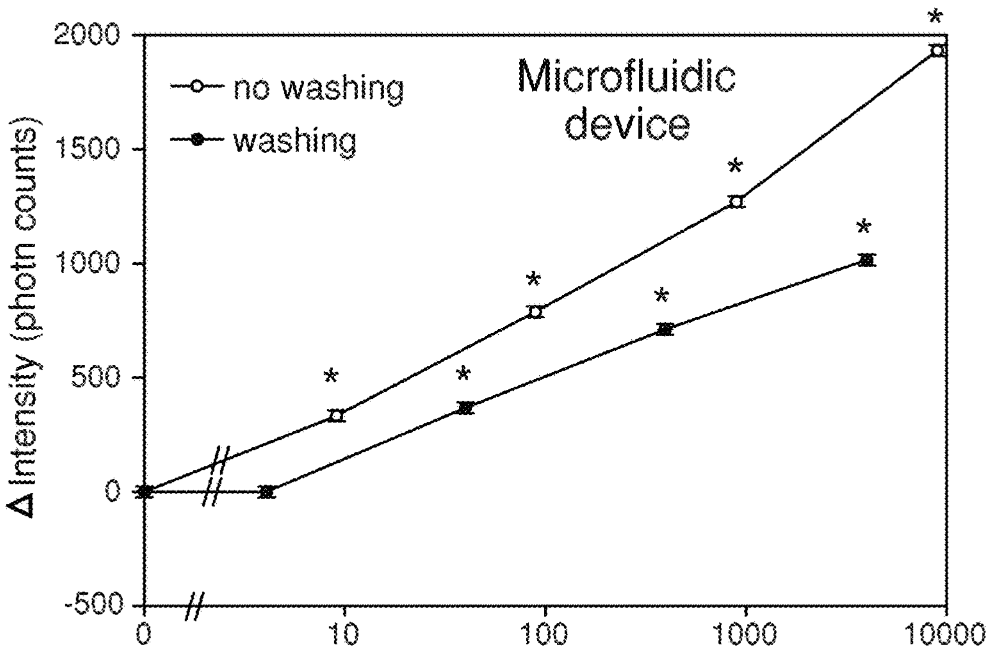
FIGS. 3A and 3B show light scattering intensities of immunoagglutinated *Escherichia coli* K-12 solutions in phosphate buffered saline (PBS) at various dilutions (a total of four different dilutions were made: $10^{-5}$, $10^{-6}$, $10^{-7}$, and $10^{-8}$ thus making standard curves), with or without washing *E. coli* was fully cultured and the viable and non-viable cell counts were evaluated using the LIVE/DEAD BacLight Bacterial Viability Kit. The viable to non-viable ratio was approximately, for example, 4:1. Dead cell fragments and free antigens were washed, for example, three times using a centrifuge, anti *E. coli* antibodies were conjugated at 33% surface coverage to 0.02% (w/v) 0.92-μm highly carboxylated polystyrene particles (>5 carboxyl groups per 1 $nm^2$ particle surface). PBS buffer was used as a negative control (blank).
Figure 3B:
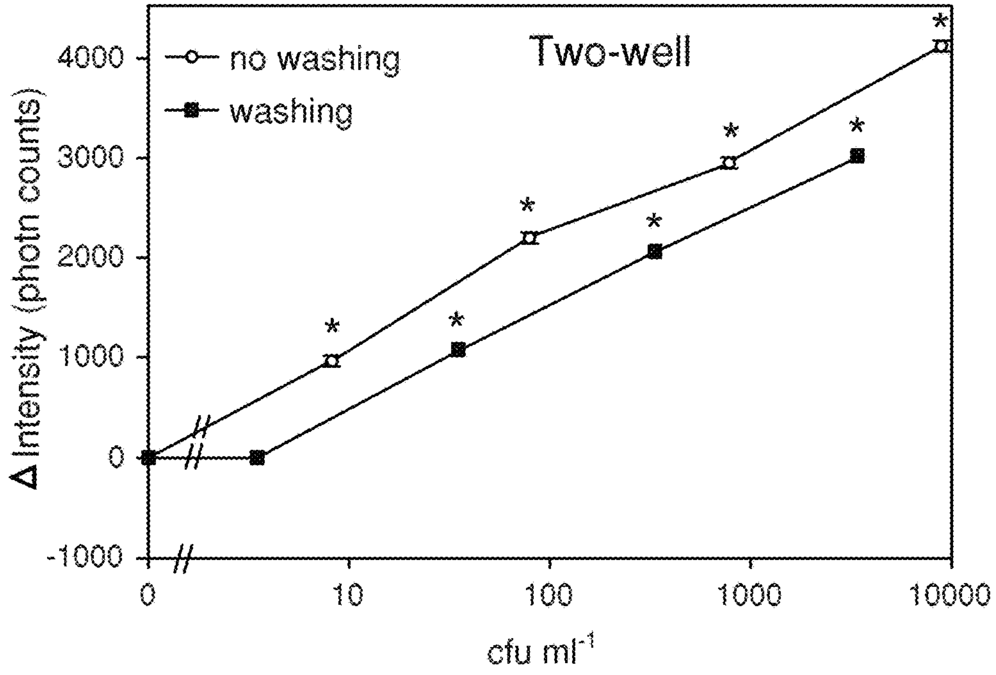
Figure 7A:
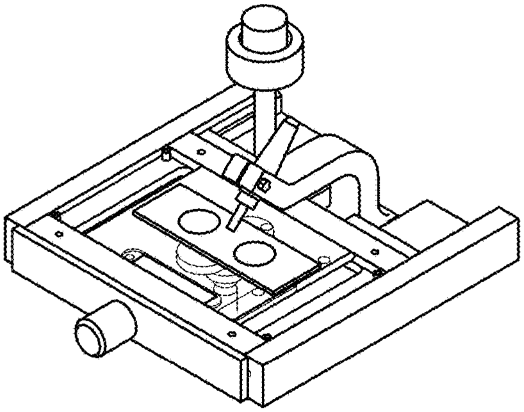
FIG. 7A shows a two-well slide (which can be replaced with a Y-channel microfluidic device.
Figure 7B:
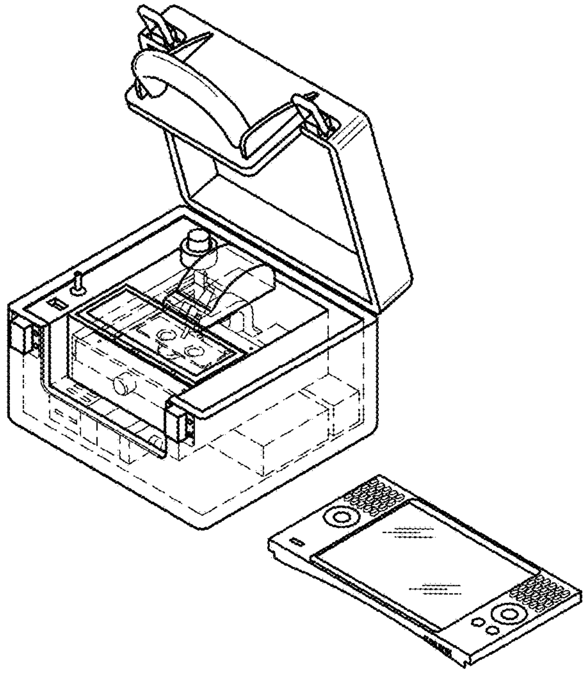
FIG. 7B shows the entire device, including a light source, a portable spectrometer, and an ultra-mobile computer communicating with a portable spectrometer.
Figure 8A:
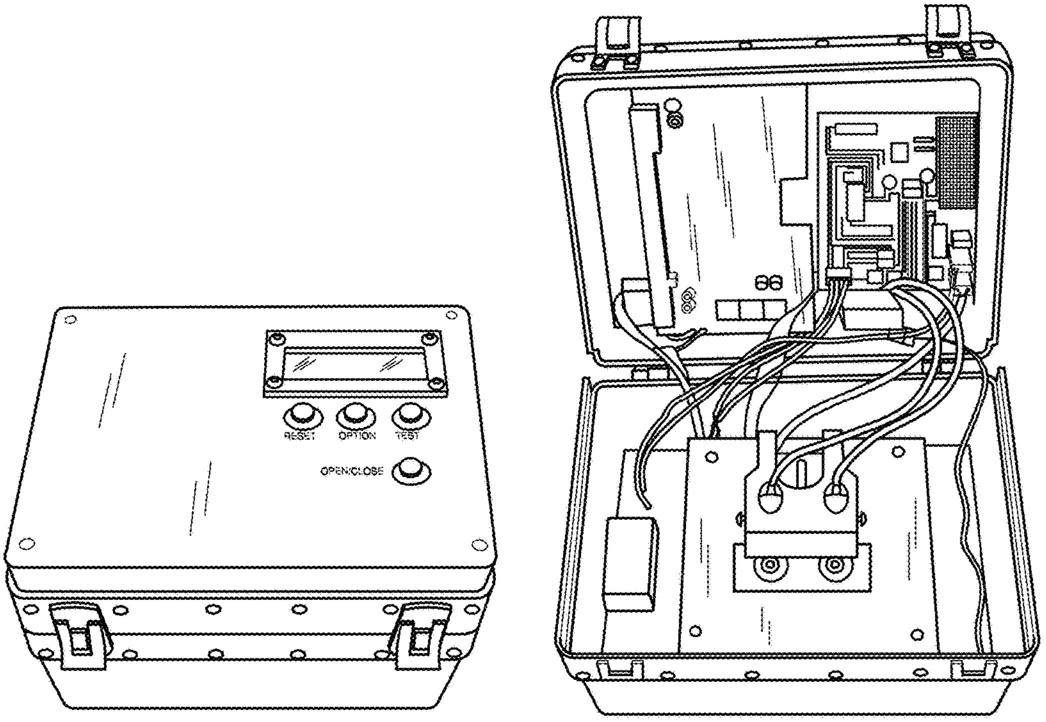
FIG. 8A shows an example of an apparatus of the present invention (e.g., an entire system, and FIG. 8B shows inner components of the apparatus in FIG. 8A.
Figure 8B:
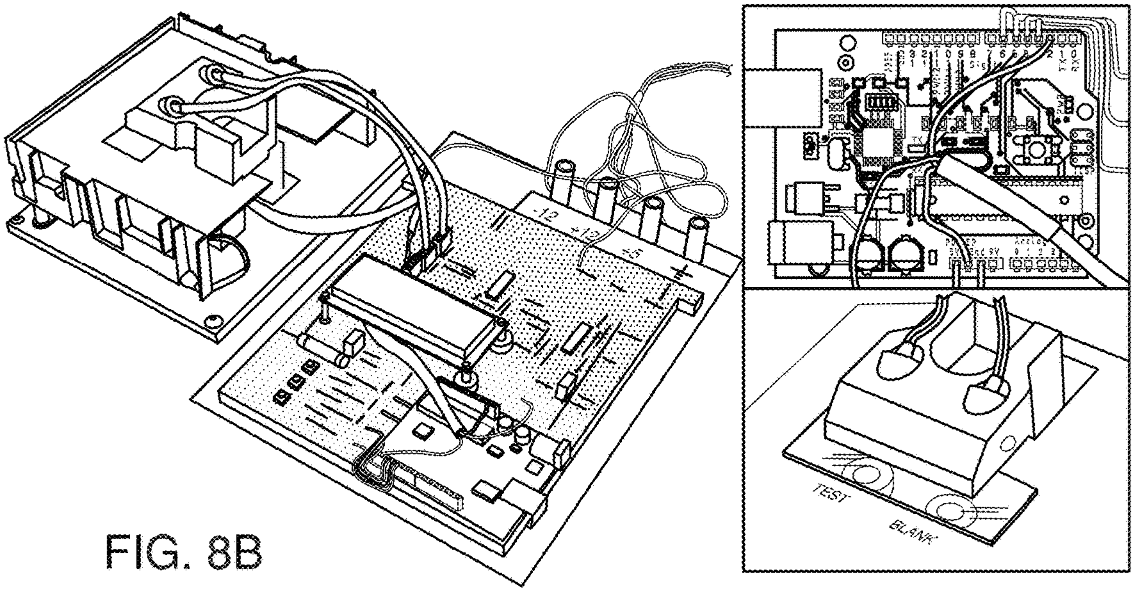
Figure 9:
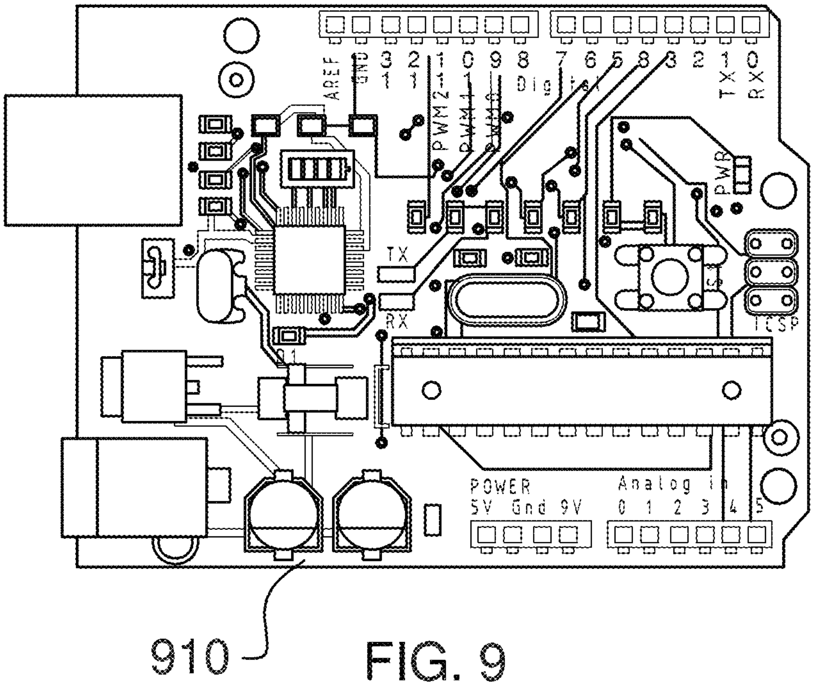
FIG. 9 is a top view of a processing unit (e.g., Arduino Duemilanove—open access and in public domain).

The present invention also features devices (or apparatuses) for detecting a microorganism in a sample. The apparatuses may be a large-scale device or a small-scale device (e.g., portable, etc.). An example of a large-scale device is shown in FIGS. 2, 7A and 7B. An example of a small-scale device is shown in FIGS. 8A and 8B.

In some embodiments, the apparatus comprises a base (e.g., a light transparent base or a base comprising a first light transparent portion/base and a second light transparent portion/base) having a first well and a second well. The first well is for holding a first mixture, the first mixture comprising a first bead suspension and a portion of the sample that potentially comprises the microorganism 105. The beads 110 in the first bead suspension, as discussed above, are conjugated with an antibody 120 specific for the microorganism 105. The second well is for holding a second mixture, the second mixture comprising a second bead suspension and a portion of the sample that potentially comprises the microorganism 105. The beads in the second bead suspension (as discussed above) are not conjugated with an antibody 120 (e.g., an antibody specific for the microorganism). In some embodiments, the number of wells in a single device can be multiplied to simultaneously obtain the results from multiple assays.

The apparatus may further comprise a first light 610*a* for irradiating the first mixture with a first incident light 605*a* and a second light 610*b* for irradiating the second mixture with a second incident light 605*b*. And, the apparatus further comprises a first detector 620*a* for detecting a first forward scattered light which is scattered by the first mixture as the first mixture is irradiated by the first incident light 605*a*, and a second detector 620*b* for detecting a second forward scattered light which is scattered by the second mixture as the second mixture is irradiated by the second incident light 605*b*. The first light 610*a* may be positioned under the first well and the second light 610*b* may be positioned under the second well. The first detector 620*a* may be disposed above the first well and the second detector 620*b* may be disposed above the second well.

The apparatus may further comprise a processing unit operatively connected to both the first detector and the second detector. The processing unit may be configured to calculate an I value from a first input signal from the first detector and an $I_0$ value from a second input signal from the second detector. The processing unit may also be configured to calculate a ratio of $I/I_0$ or a difference between I and $I_0$.

A display component displays I and $I_0$ and/or the ratio of $I/I_0$ and/or the difference between I and $I_0$. A power source may be operatively connected to the first light 610*a*, the first detector 620*a*, the second light 610*b*, the second detector 620*b*, and the processing unit. In some embodiments, the apparatus further comprises a USB interface for either programming or retrieving data. USB interfaces are well known to one of ordinary skill in the art. In some embodiments, the USB interface is used to retrieve data from previous assays (e.g., stored data).

The entire assay can also be performed on a microfluidic device 160 using the same light source and detector configurations. An example of this is shown in FIG. 1A. The microfluidic device 160 may have a Y-shaped configuration with two inputs that meet at a vertex. The solutions added to the inputs are mixed at the vertex. The microfluidic device 160 with the Y-shaped configuration may provide a continuous analysis of samples (versus a stagnant analysis). In some embodiments, two identical Y-channels are needed in a single device to simultaneously measure I and $I_0$. In some embodiments, the number of Y-channels in a single device can be multiplied to simultaneously obtain the results from multiple assays.

Operational Amplifier Circuit and Processing Unit

In some embodiments, the processing unit comprises an operational amplifier (op-amp) circuit configured to amplify the signals produced by the first and second detectors, respectively. Op-amps are well known to one of ordinary skill in the art. In some embodiments, the op-amps are configured to generate the I value from the first input signal from the first detector and the $I_0$ value from the second input signal from the second detector. In some embodiments, the op-amps are configured to calculate a ratio of $I/I_0$ or a difference between I and $I_0$. In some embodiments, the op-amps comprise or are operatively connected to an analog-digital converter, wherein the analog-digital converter converts an analog input from the operational amplifier circuit to a digital signal and sends the digital signal to the display.

In some embodiments, the processing unit is an Arduino 910 (e.g., Arduino Duemilanove, see FIG. 9), which is open access thus in public domain. In some embodiments, the power source is one or more batteries (e.g., one or more 9-volt batteries).

In some embodiments, the light 610*a*, 610*b* is a light emitting diode or a laser diode (e.g., with collimating lens). In some embodiments, the light 610*a*, 610*b* emits a light with a wavelength of about 650 nm. In some embodiments, the light 610*a*, 610*b* emits a light with a wavelength of between about 320-800 nm. In some embodiments, the detector 620*a*, 620*b* is a photodiode [e.g., Avalanche photodiode (APD)]. In some embodiments, the operational amplifier is a quadruple op-amp LM324.

Slides and Wells

Figure 10:
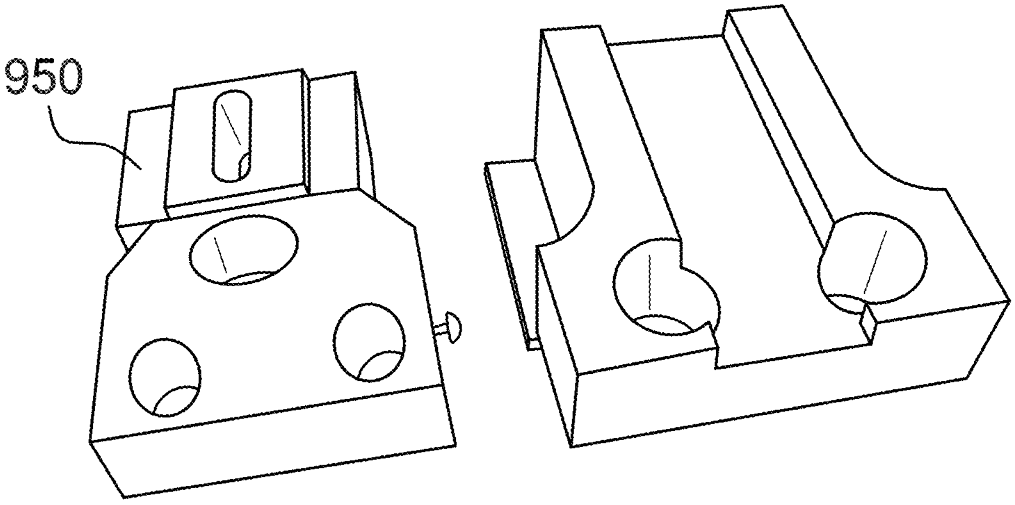
FIG. 10 is a perspective view of positioning stages that may be used in the apparatuses of the present invention.
Figure 11:
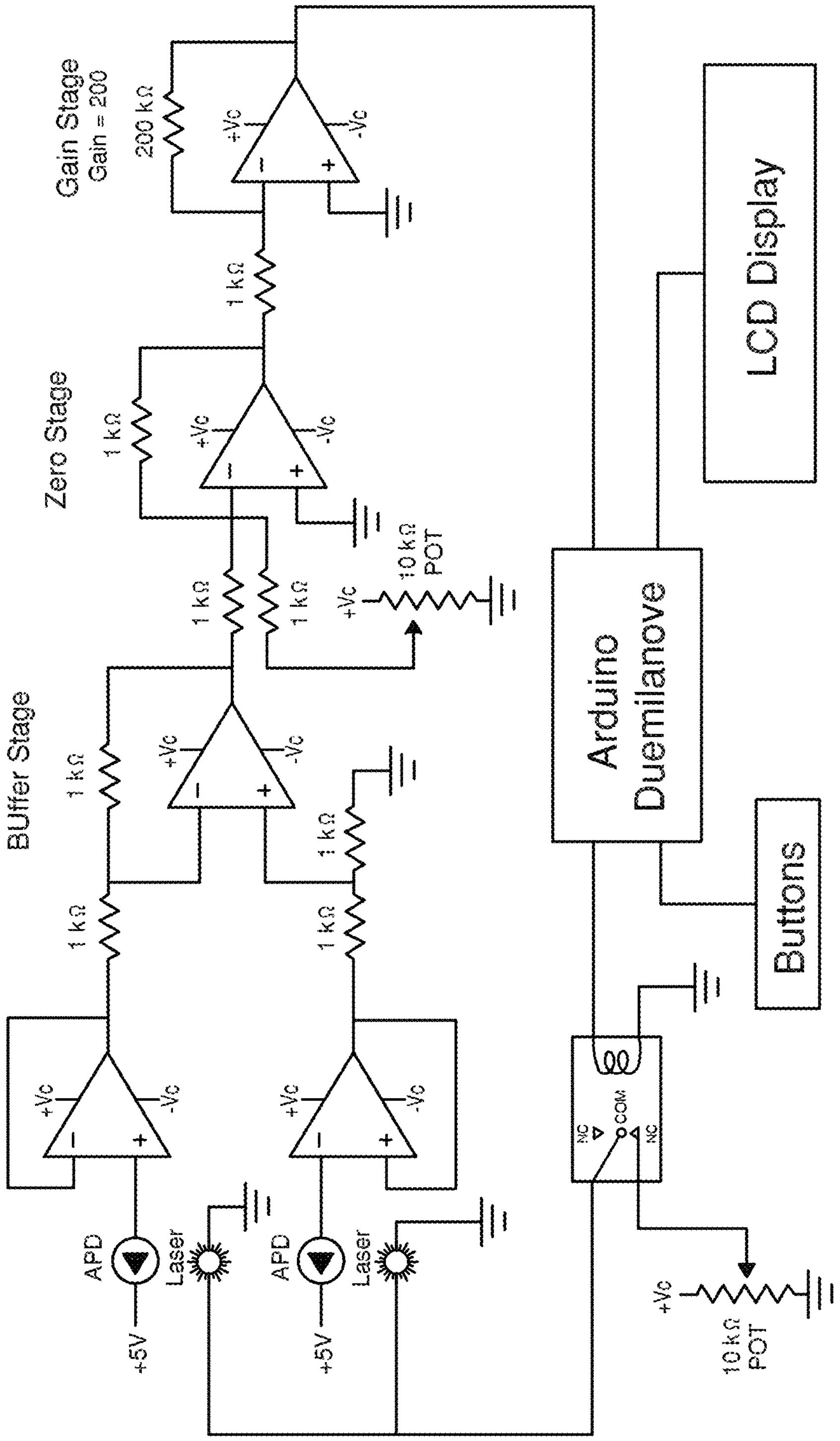
FIG. 11 is a schematic representation of the electrical circuit components (op-amp circuit) of an embodiment of the apparatuses of the present invention.
Figure 12A:
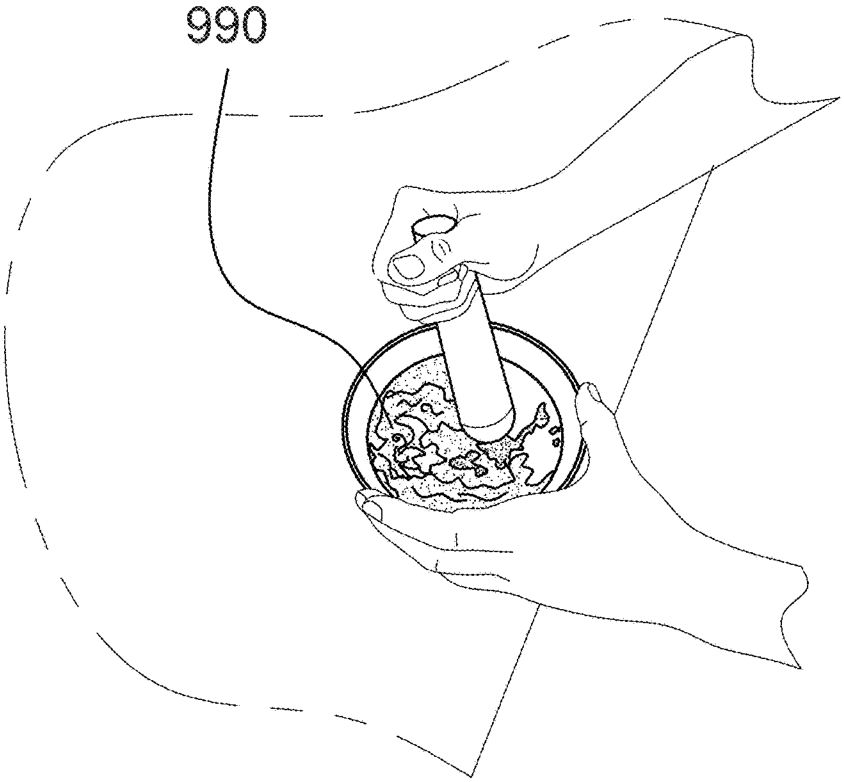
FIGS. 12A, 12B, and 12C show examples of sample preparation.
Figure 12B:
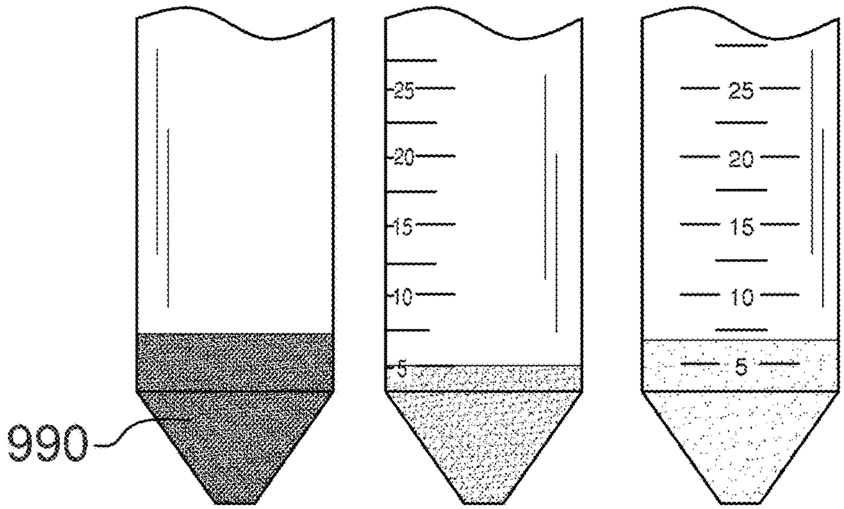
Figure 12C:
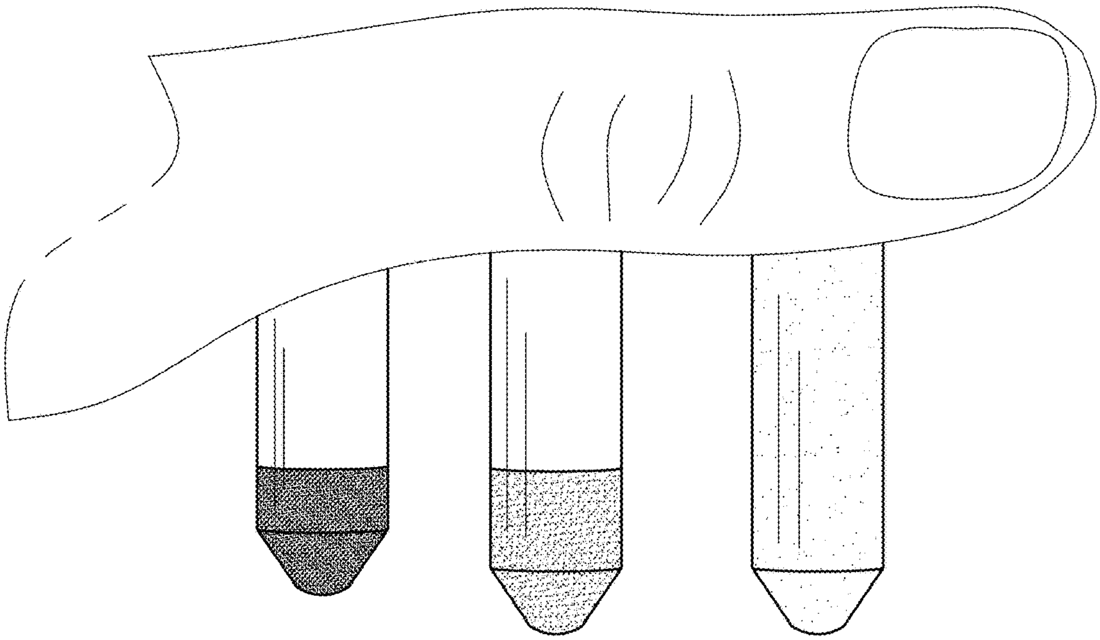
Figure 13A:
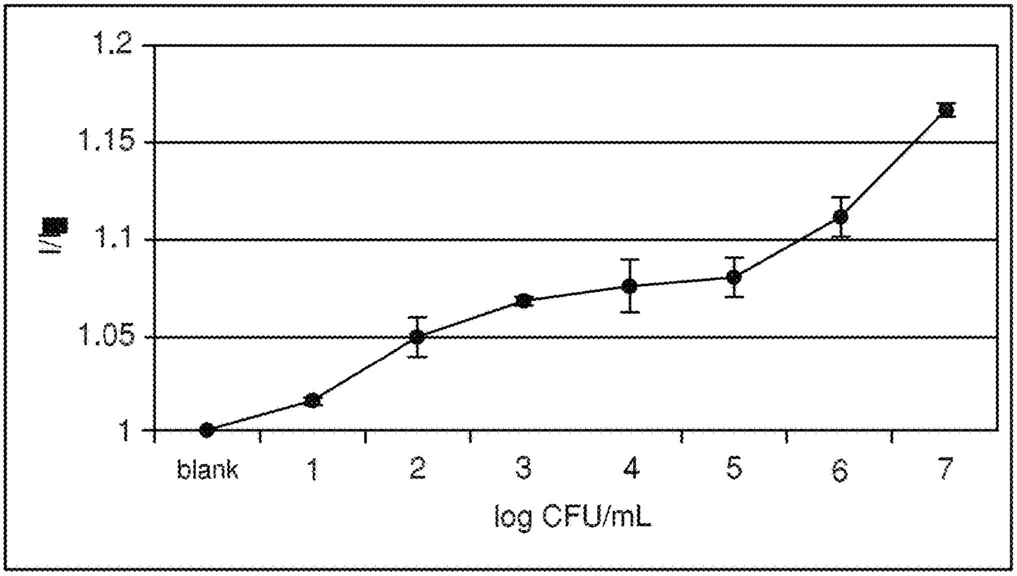
FIG. 13A shows an example of $I/I_0$ for *E. coli* in iceberg lettuce. The measurements were performed via a large-scale system (e.g., FIG. 2), which includes a miniature spectrometer, fiber optics, and adjustable positioning stages
Figure 13B:
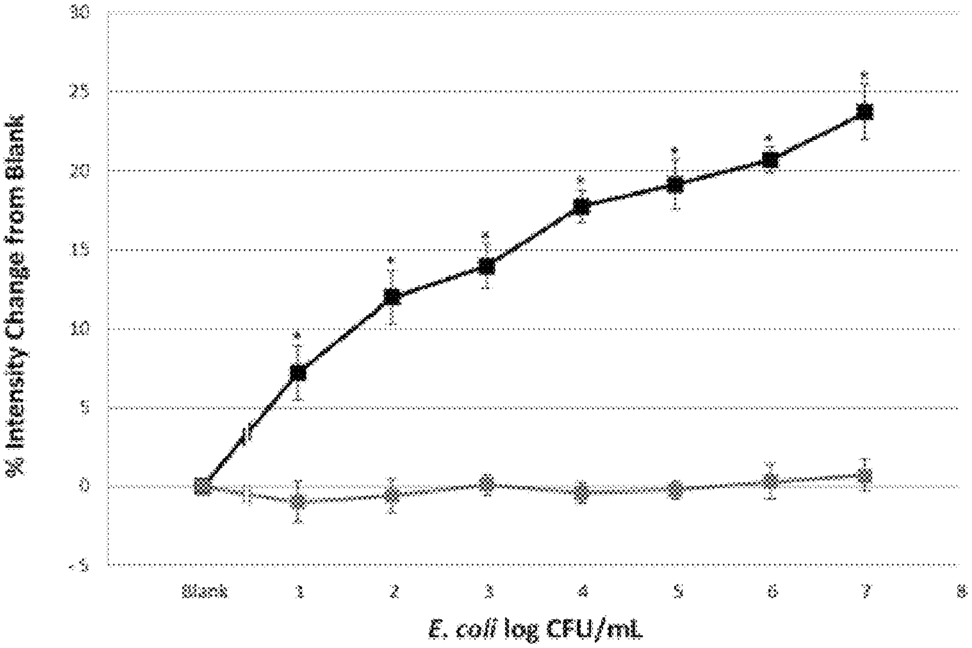
FIG. 13B shows an example of $I/I_0$ for *E. coli* in iceberg lettuce. The measurements were performed via a small-scale system (e.g., FIGS. 8A and 8B), which includes a laser diode, Avalanche photodiode, fixed positioning stage, op-amp circuit and Arduino board.

In some embodiments, the slides and/or wells are installed on adjustable positioning stages (e.g., FIG. 2) or fixed positioning stages 950 (e.g., FIG. 10). In some embodiments, the first well and the second well are constructed from a material comprising a microscope glass slide. The first well and the second well may have a diameter of about 18 mm. Or, in some embodiments, the first well and the second well have a diameter between about 2 to 30 mm.

In some embodiments, the first well and the second well have a depth of about 800 μm. In some embodiments, the first well and the second well have a depth between about 100 to 1,500 μm.

In some embodiments, the lights and/or detectors are mounted on plastic fabricated by a milling machine or a rapid prototyping device.

Statistical Analysis

A ratio of $I/I_0$ can be calculated via the apparatuses of the present invention. In some embodiments, a ratio of greater than 1 indicates the presence of the microorganism in the sample. Means (m) and standard deviations (σ) of $I/I_0$ can be collected from multiple measurements. Two-sigma bounds (m−2σ, m+2σ) can be obtained, wherein the lower bound (m−2σ)>1 indicates that $I/I_0$ is greater than 1 with a 95% confidence level.

A difference between I and $I_0$ can be calculated by subtracting of $I_0$ from of I. In some embodiments, a difference of greater than 0 indicates the presence of the microorganism in the sample. As stated above, means (m) and standard deviations (σ) can be collected from multiple measurements. Two-sigma bounds (m−2σ, m+2σ) can be obtained, wherein the lower bound (m−2σ)>0 indicates that $I-I_0$ is greater than 0 with a 95% confidence level.

Optimization

In some embodiments, the distance between the well or sample and the light or detector is fixed. Or, in some embodiments, the focal point is fixed or the angle is fixed. In some embodiments, the apparatus allows for manipulation (or fine tuning) of the distance between the well or sample and the light or detector, or the focal point can be manipulated, or the angle can be manipulated.

EXAMPLES

Example 1

Conjugation of an Antibody

The following is an example of conjugating an antibody. The present invention is not limited to this example. One (1) ml of 0.02% (w/v) 0.92-μm highly carboxylated polystyrene (HCPS) particles (e.g., 10 carboxyl groups per 1 $nm^2$ particle surface; Bangs Laboratories, Fishers, Ind.) can be conjugated with 1 ml of 1.023 μg/ml anti-*E. coli* (e.g., polyclonal antibody developed in rabbit; catalog number ab13626; Abcam, Cambridge, Mass.) via physical adsorption. Surface coverage of antibodies to particles may be about 33%.

Example 2

Culturing of *Escherichia Coli*

The following is an example of culturing *Escherichia* coli. The present invention is not limited to this example. *E. coli* K-12 lyophilized cell powder (Sigma-Aldrich catalog number EC1) can be cultured in media, for example brain heart infusion broth (Remel, Lenexa, Kans.), at about 37° C. for about 20 h. The grown cell culture of lyophilized *E. coli* K-12 can be serially diluted with 10 mM PBS (pH 7.4) by $10^{-5}$ to $10^{-8}$. As the lyophilized powder of *E. coli* K-12 may contain dead cell fragments and free antigen, the diluted *E. coli* K-12 solutions can be washed by centrifuging at about 2000 g for about 15 min, followed by elimination of supernatants and resuspension in PBS. This centrifugation-resuspension can be repeated (e.g., 3 times) to help ensure complete removal of dead cell fragments and free antigens.

A viable cell count can be performed by planting dilutions (e.g., abut 200 μl) to eosin methylene blue agar (DIFCO, Lawrence, KS) and incubating at about 37° C. for about 20 h. To stain viable and non-viable cells, SYTO 9 and propidium iodide (LIVE/DEAD BacLight viability kit; Invitrogen, Carlsbad, Calif.) can be used following the protocol as described in manufacturer's product information (Molecular Probes, 2004). Stained *E. coli* cells can be observed with a fluorescent microscope (Nikon, Tokyo, Japan). Cells can be counted using a Petroff-Hausser counting chamber (Electron Microscopy Sciences, Hatifield, Pa.).

Example 3

Fabrication of a Microfluidic Device

Figure 1B:
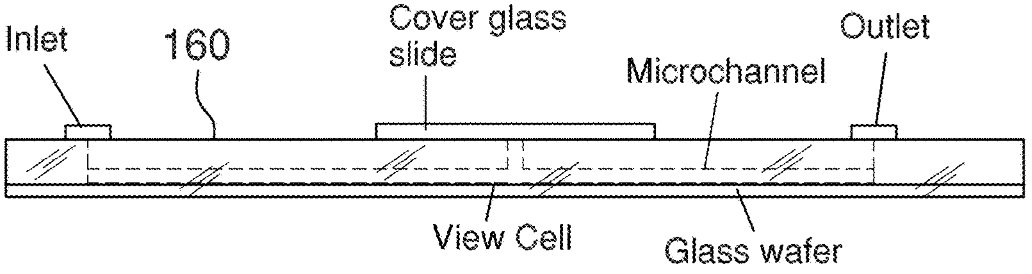
FIG. 1B is a side cross sectional view of an example of a microfluidic device.

The following is an example of fabrication of a microfluidic device according to the present invention. The present invention is not limited to this example. Microfluidic devices can be fabricated via standard soft lithography with a polydimethyl siloxane (PDMS) molding technique (well known to one of ordinary skill in the art). An example of a layout of a Y-shaped microfluidic device is shown in FIGS. 1A and 1B. The microfluidic device may comprise a slide (e.g., PDMS slide) with a first inlet (e.g., well) and a second inlet (e.g., well). The inlets (e.g., first inlet/well, second inlet/well) may be constructed to have a dimension of about 200 μm (width)×100 μm (depth) as measured by a profilometer (Alpha Step 2000, Tencor Instruments, Reston, Va.). In some embodiments, the inlets/wells may be constructed to have other dimensions.

In some embodiments, a second slide (e.g., PDMS slide) can be used as a cover in order to get a sufficient light path length (800 μm) in the view cell; however, this in some cases may make it difficult to acquire strong light scattering signals. In some embodiments, a hole can be made (e.g., diameter of about 2 mm; depth of about 2 mm) through the PDMS channel (e.g., using a hole puncher) to produce a view cell. Glass slides (e.g., the second slide, a third slide) can be bound on both top and bottom sides of the view cell, for example using oxygen plasma asher (Plasma Preen Cleaner/Etcher; Terra Universal, Fullerton, Calif.) at about 550 W for about 20 s (see FIG. 1B). The plasma bonding procedure can also make the PDMS hydrophilic, which can remain hydrophilic from about 24 h to about one week. This layout can produce a sufficient light path length, which may enhance the signal. The two inlets and one outlet can be then connected via Teflon® tubes (e.g., 0.79 mm OD; Upchurch Scientific, Oak Harbor, Wash.).

Example 4

Detection of Light Scattering

The following is an example of the detection of light scattering. The present invention is not limited to this example. FIG. 2 shows an example of an experimental setup for detecting light scattering using a microfluidic device according to the present invention. The setup comprises a spectrometer (e.g., a USB4000 miniature spectrometer), a light source (e.g., a model LS LED light source), and fiber optic cables (Ocean Optics, Dunedin, Fla.). The setup can be arranged in what is known as "proximity" fiber arrangement, for example the fiber distal ends are both very close (e.g., 1 mm) but not touching the microfluidic device. The two optical fibers for lighting and detection in the example have a 600 μm core diameter and 30 μm cladding with optimal transmission in the UV-visible wavelengths. The fibers are 1.0 meter in length with SMA-905 connectors (probes) on each end. The numerical aperture of these optical fibers and probes is 0.22 with an acceptance angle of about 25°. The 380 nm wavelength UV LED supplies about 45 μW power to the optical fiber assembly. The second fiber is positioned as a detector above the chip at about a 45° angle to measure light scattering while avoiding any of the direct incident light beam.

A syringe pump (KD Scientific, Holliston, Mass.) can be used to inject beads (e.g., microparticles) conjugated with anti-*E. coli* and samples (e.g., *E. coli* target solutions) to the Y-junction microchannel. Two Teflon® tubes (0.79 mm OD) can connect two 250-μl gastight syringes (Hamilton, Reno, Nev.) to the top openings of the PDMS substrate.

In some embodiments, two-well glass slides (model 48333, VWR, West Chester, Pa.) can be used (see FIG. 1A). These slides have two polished spherical depressions of about 18 mm diameter and about 800 μm depth. These may potentially lead to stronger signal.

Example 5

Vegetable Sample Preparation

The following is an example of vegetable sample preparation. The present invention is not limited to this example. Iceberg lettuce 990 is chopped up using a grinding bowl (see FIG. 12A). Phosphate buffered saline (PBS; 100 mM) is added to this chopped iceberg lettuce 990 at the ratio of 2:1 (buffer:lettuce) (see FIG. 12B). If the lettuce is not contaminated with *E. coli*, a known amount of *E. coli* may be added to PBS. This mixture is loaded in a 1 ml disposable syringe. KimWipes, delicate task wiper, is placed onto the outlet of a syringe, without a needle. Big vegetable particles (but not *E. coli*) are filtered with KimWipes, by injecting the plunger of a syringe (see FIG. 12C). The filtered sample is loaded into a two-well slide or a Y-channel microfluidic device.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A method of detecting *Escherichia coli* (*E. coli*) in a vegetable sample using a portable microfluidic device, the vegetable sample comprising a vegetable component in a buffer, the method comprises:

mixing via diffusional mixing in a first well of a light transparent base of the portable microfluidic device both a first bead solution and a portion of the vegetable sample to create a first mixture, the first bead suspension comprises beads conjugated with an antibody specific for *E. coli*, the beads are constructed from a material comprising polystyrene and comprise a plurality of carboxyl groups disposed on an outer surface and have a diameter of 920 nm;

mixing via diffusional mixing in a second well of the light transparent base of the portable microfluidic device both a second bead solution and a portion of the vegetable sample to create a second mixture, the second bead suspension comprises beads that are not conjugated with the antibody specific for *E. coli*, the beads are constructed from a material comprising polystyrene and comprise a plurality of carboxyl groups disposed on an outer surface and have a diameter of 920 nm;

irradiating the first well and the second well with incident light using a light disposed under the first well and the second well, the incident light having a wavelength of 650 nm;

detecting using a detector forward scattered light at a 45 degree angle with respect to the incident light scattered by the first mixture and forward scattered light at a 45 degree angle with respect to the incident light scattered by the second mixture, the detector is operatively connected to a processing unit, the processing unit comprises an operational amplifier circuit and calculates I from the forward scattered light scattered by the first mixture and calculates $I_0$ from the forward scattered light scattered by the second mixture, the processing unit compares I with $I_0$ by either calculating a ratio of $I/I_0$ or calculating a difference between I and $I_0$ by subtracting of $I_0$ from of I; and determining if *E. coli* is present in the sample, wherein a ratio of $I/I_0$ greater than 1 indicates the presence of *E. coli* in the sample or a difference in I and $I_0$ greater than 0 indicates the presence of *E. coli* in the sample.

2. The method of claim 1, wherein the beads in the first bead solution and the second bead solution comprise at least 5 carboxyl groups per $nm^2$ surface area.

3. The method of claim 1, wherein the carboxyl groups are polyacrylic acid (PAA) or polymethacrylic acid (PMAA).

* * * * *